(12) United States Patent
Bohlander

(10) Patent No.: US 6,278,003 B1
(45) Date of Patent: Aug. 21, 2001

(54) PROCESS FOR REFINING EPOXY COMPOUNDS, AND HEAT-STABLE EPOXY COMPOUNDS PREPARED THEREBY

(75) Inventor: Ralf Bohlander, Duesseldorf (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/530,675

(22) PCT Filed: Oct. 24, 1998

(86) PCT No.: PCT/EP98/06765

§ 371 Date: Jun. 27, 2000

§ 102(e) Date: Jun. 27, 2000

(87) PCT Pub. No.: WO99/23085

PCT Pub. Date: May 14, 1999

(30) Foreign Application Priority Data

Nov. 4, 1997 (DE) .............................................. 197 48 573

(51) Int. Cl.[7] .................................................. C07D 301/32
(52) U.S. Cl. ............................................. 549/542; 549/541
(58) Field of Search ..................................... 549/542, 541

(56) References Cited

U.S. PATENT DOCUMENTS

| | | | |
|---|---|---|---|
| 3,436,377 | 4/1969 | Dittman et al. ..................... | 260/78.4 |
| 4,423,239 | 12/1983 | Miyazaki et al. ..................... | 549/541 |
| 4,772,732 | 9/1988 | Huang et al. ......................... | 549/542 |

FOREIGN PATENT DOCUMENTS 30 02 861 C2  11/1981 (DE) .

OTHER PUBLICATIONS

Chemical Abstracts, vol. 76, No. 2, Jan. 10, 1972, Columbus, Ohio, US; Abstract No. 4304, Dittmann: "Effect of microstructure on the epoxidation of liquid polybutadiene", XP002094892 & *Chemiker–Zeitung*, 95. Jahrgang (1971) Nr. 15/16, pp. 684–692.

Findley, et al., Epoxidation of Unsaturated Fatty Materials with Peracetic Acid in Glacial Acetic Acid Solution, *J.Am. Chem.Soc.*, vol. 67, (Mar., 1945), pp. 412–414.

Swern, et al., "Epoxidation of Oleic Acid, Methyl Oleate and Oleyl Alcohol with Perbenzoic Acid", *J.Am.Chem.Soc.*, vol. 66, (Nov., 1944), pp. 1925–1927.

*Primary Examiner*—Ba K. Trinh
(74) *Attorney, Agent, or Firm*—John E. Drach; Aaron R. Ettelman

(57) ABSTRACT

A process for refining epoxy compounds, wherein the process comprises: (a) providing a washed and dried organic phase comprising at least one epoxide compound; (b) contacting the organic phase with at least one basic solid selected from the group consisting of aluminum oxides, aluminum hydroxides and alkali metal silicates; and (c) separating the organic phase and the at least one basic solid, is disclosed.

14 Claims, No Drawings

PROCESS FOR REFINING EPOXY COMPOUNDS, AND HEAT-STABLE EPOXY COMPOUNDS PREPARED THEREBY

This application is a 371 of PCT/EP98/06765, dated Oct. 24, 1998.

BACKGROUND OF THE INVENTION

Epoxy compounds have a wide field of application in the production of plastics, polymer foams, surface coatings, and coating materials. It is desirable for these substances to have a very high epoxy oxygen content, and at the same time the volatile component content must be as low as possible in order to prevent exudation (fogging) on the plastics parts. Finally, the products must be sufficiently heat-stable; i.e., at relatively high temperatures as encountered during the preparation of the polymers, there must be no unwanted crosslinking of the epoxides with one another and no increase in viscosity.

From the prior art it is known to subject epoxy compounds prepared by the performic acid process to neutral washing by repeated treatment with water or aqueous alkali and to remove catalyst residues together with the washing water. Normally, this is followed by the phases being separated, the washing water being stripped off or removed by centrifugation, and the residual moisture content in the product being removed by adding sodium sulfate or by vacuum drying. Alternatively, traces of acid can be removed from the epoxides by introducing gaseous ammonia, by neutralization with anhydrous sodium carbonate, by azeotropic distillation, or by the use of anion exchangers [cf. Chem. Ztg. 95, 684(1971)].

Although the measures of the prior art, and especially the known method of wet refining with alkali metal hydroxide solution, make it possible to reduce the number of washing steps, it is nevertheless the case that under these conditions, from epoxidized esters, for example, surface-active soaps having emulsifying properties may be formed, and phase separation is therefore retarded. At the same time, there is increased incidence of epoxy ring opening reactions, which reduce the epoxy oxygen content.

The object of the invention was therefore to provide a process for preparing heat-stable epoxides which is free from the disadvantages depicted.

BRIEF SUMMARY OF THE INVENTION

The present invention includes a process for preparing heat-stable epoxy compounds wherein epoxide compounds are washed, dried, treated with selected basic solids and filtered.

The invention provides a process for preparing heat-stable epoxy compounds in which olefinically unsaturated compounds are epoxidized in a manner known per se and the resulting oxirane compounds a) are washed with water and/or aqueous alkali solution, and b) the useful, organic phase is separated off and dried, which comprises subsequently treating the useful organic phase with solid, basic aluminum oxides, aluminum hydroxides and/or alkali metal silicates and filtering it.

It has surprisingly been found that the epoxy compounds obtained in this way rather than by prior art workup processes have a higher epoxy oxygen content even after thermal exposure and have a reduced tendency to crosslink during storage and to develop an unwanted viscosity. At the same time, the proposed process reduces the number of washing steps, which results in a technical simplification and reduces the amount of wastewater. Furthermore, the invention includes the finding that higher yields are obtained when the epoxy compounds obtainable by the process of the invention are worked up by distillation.

DETAILED DESCRIPTION OF THE INVENTION

Epoxy Compounds

The selection of the epoxides to which the process of the invention can be applied is not critical per se. Preference is given to the use of epoxides of olefinically unsaturated fatty substances, such as, for example, epoxides of olefinically unsaturated triglycerides, fatty acid lower alkyl esters (i.e., esters of fatty acids having 6 to 22 carbon atoms with alcohols having 1 to 8 carbon atoms) and/or fatty alcohols. Particular preference is given to the use of epoxidized triglycerides based on soybean oil, linseed oil, rapeseed oil, sunflower oil, tall oil, cottonseed oil, groundnut oil, palm oil, or neat's-foot oil, it having been found optimal in terms of the color quality of the products to use epoxides having a high degree of epoxidation and a low iodine number. Epoxidized triglycerides are known substances which are used in other technical fields as so-called "epoxy plasticizers". They are prepared by epoxidizing unsaturated fats and oils by the so-called "in situ performic acid process", which is described in J. Am. Chem. Soc. 67, 412 (1945). Depending on the amount of peracid used, epoxidation converts some or all of the olefinic double bonds of the glyceridically linked fatty acids to oxirane rings. Particularly suitable are triglycerides having an iodine number in the range from 50 to 150, which on substantial epoxidation of the olefinic double bonds are converted to epoxides having an epoxy oxygen content of from 3 to 10% by weight. For technical reasons, preference is given to the use of epoxidized soybean oil and/or epoxidized soya fatty acid methyl ester. On the preparation of epoxidized fatty alcohols, cf. also D. Swern in J. Am. Chem. Soc. 66, 1925 (1944). In addition to the epoxidized fatty substances, which to a certain extent represent functionalized olefins, it is of course also possible to use conventional epoxidized olefins having 6 to 18 carbon atoms, whose epoxide group is either at the end or in the interior of the molecule. Typical examples are $\alpha$-epoxides of decene, dodecene, tetradecene, hexadecene and octadecene, and of corresponding technical-grade mixtures of these olefins.

Basic Solids

For the refining of the epoxides, suitable basic solids include aluminum oxides, aluminum hydroxides and also alkaline silicates such as, for example, Primisils, Celatoms or Celites. The amount of these substances used can be from 0.5 to 5, preferably from 1 to 3% by weight, based on the epoxides.

Refining

To refine the epoxides they are first of all washed, one particularly advantageous embodiment of the process of the invention consisting in treating the substances only once or twice with an equal amount by weight of water or alkali solution. Washing more times than this, as described in the prior art, is unnecessary from the standpoint of further refining. The term "alkali solution" is to be understood as referring, for example, to aqueous sodium hydroxide or sodium carbonate solutions having a solids content in the range from 1 to 15% by weight. After washing, phase separation takes place by decanting, the useful organic phase being dried in a manner known per se. Subsequently, the basic solids are added and, after stirring, the mixture is filtered until the product appears to be pure.

EXAMPLE

Epoxidized soybean oil was purified by the following processes:

(P1) Washing 5 times with an equal amount by weight of water, phase separation, and vacuum drying of the organic phase.

(P2) Washing 5 times with an equal amount by weight of water, then washing with an equal amount by weight of 2% strength by weight sodium hydroxide solution, phase separation, and vacuum drying of the organic phase.

(P3) Washing 5 times with an equal amount by weight of water, then washing with an equal amount by weight of 2% strength by weight sodium carbonate solution, phase separation, and vacuum drying of the organic phase.

(1) Washing twice with an equal amount by weight of water, phase separation, vacuum drying of the organic phase, addition of 0.5% by weight of basic aluminum oxide hydrate, and filtration.

Subsequently, the epoxy oxygen content and the Brookfield viscosity (RVT viscometer, 20° C., spindle 1, 10 rpm) was determined immediately and after storage at 150° C. for 24 h. The results are collated in Table 1. Example 1 is in accordance with the invention, Examples P1 to P3 serve for comparison.

TABLE 1

Stability and viscosity

| Properties | P1 | P2 | P3 | 1 |
|---|---|---|---|---|
| Epoxy oxygen content [% by wt.] | | | | |
| immediate | 6.65 | 6.55 | 6.75 | 6.85 |
| after 24 h, 150° C. | 6.25 | 6.20 | 6.45 | 6.70 |
| Viscosity [mPas] | | | | |
| immediate | 580 | 580 | 585 | 590 |
| after 24 h, 150° C. | 880 | 760 | 650 | 630 |

What is claimed is:

1. A process for refining fatty-epoxy compounds, said process comprising:
   (a) providing a washed and dried organic phase comprising at least one epoxide of an olefinically unsaturated fatty substance;
   (b) contacting the organic phase with at least one basic solid selected from the group consisting of aluminum oxides, aluminum hydroxides and alkali metal silicates; and
   (c) separating the organic phase and the least one basic solid.

2. The process according to claim 1, wherein the olefinically unsaturated fatty substance is selected from the group consisting of triglycerides, fatty acid lower alkyl esters, fatty alcohols, and mixtures thereof.

3. The process according to claim 1, wherein the at least one epoxide is selected from the group consisting of epoxidized soybean oil, epoxidized soya fatty acid methyl ester and mixtures thereof.

4. The process according to claim 1, wherein the at least one epoxide comprises an epoxidized olefin having from about 6 to about 18 carbon atoms.

5. The process according to claim 4, wherein the at least one epoxide comprises a terminal epoxidized olefin and an internal epoxidized olefin, each olefin having from about 6 to about 18 carbon atoms.

6. The process according to claim 1, wherein the organic phase is washed up to about two times with an equal amount by weight of water and/or an aqueous alkali solution.

7. The process according to claim 6, wherein the aqueous alkali solution is selected from sodium hydroxide and sodium carbonate.

8. The process according to claim 1, wherein the basic solid is present in an amount of from about 0.5 to about 5% by weight, based on the amount of the at least one epoxide.

9. The process according to claim 1, wherein the basic solid is present in an amount of from about 1 to about 3% by weight, based on the amount of the at least one epoxide.

10. The process according to claim 8, wherein the basic solid comprises an aluminum oxide hydrate.

11. The process according to claim 1, wherein the organic phase and the at least one basic solid are separated by filtration.

12. The process according to claim 1, wherein the organic phase is washed twice with an equal amount by weight of water, phase separated and vacuum dried.

13. A process for refining epoxy compounds, said process comprising:
   (a) providing an organic phase comprising at least one of an olefinically unsaturated fatty substance, washing the organic phase twice with equal amount by weight of water, phase separating water and the organic phase, and vacuum drying the organic phase, to provide a washed and dried organic phase;
   (b) contacting the washed and dried organic phase with at least one basic solid selected from the group consisting of aluminum oxides, aluminum hydroxides and alkali metal silicates, to form a basic sold/organic phase mixture; and
   (c) filtering the basic solid/organic phase mixture to remove the at least one basic solid.

14. A heat-stable epoxy compound prepared by a process comprising providing a washed and dried organic phase comprising at least one epoxide of an olefinically unsaturated fatty substance; containing the organic phase with at least one basic solid selected from the group consisting of aluminum oxides, aluminum hydroxides and alkali metal silicates; and separating the organic phase and the at least one basic solid.

* * * * *